(12) United States Patent
McClane et al.

(10) Patent No.: US 7,039,452 B2
(45) Date of Patent: **\*May 2, 2006**

(54) METHOD AND APPARATUS FOR RAMAN IMAGING OF MACULAR PIGMENTS

(75) Inventors: Robert W. McClane, Salt Lake City, UT (US); Werner Gellermann, Salt Lake City, UT (US); Paul S. Bernstein, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 616 days.

This patent is subject to a terminal disclaimer.

(21) Appl. No.: 10/040,883

(22) Filed: Jan. 7, 2002

(65) Prior Publication Data
US 2003/0130579 A1    Jul. 10, 2003

(51) Int. Cl.
*A61B 5/05*    (2006.01)

(52) U.S. Cl. ............... 600/424; 600/407; 600/473; 600/475; 600/476; 600/477; 600/478; 356/301; 356/303; 606/2; 606/3; 606/4; 606/10

(58) Field of Classification Search ........... 600/407, 600/473, 475, 476, 477, 478, 322, 424, 310, 600/318; 356/301, 303; 606/2–4, 10
See application file for complete search history.

(56) References Cited

U.S. PATENT DOCUMENTS

| | | | |
|---|---|---|---|
| 4,144,464 A | 3/1979 | Loree et al. | 307/88.3 |
| 4,318,057 A | 3/1982 | Buchwald et al. | 372/70 |
| 4,500,995 A | 2/1985 | White | 372/3 |
| 4,758,081 A | 7/1988 | Barnes | 351/221 |
| 4,807,240 A | 2/1989 | Goldstone | 372/69 |
| 4,832,483 A * | 5/1989 | Verma | 600/322 |
| 4,852,579 A | 8/1989 | Gilstad et al. | 128/665 |

(Continued)

FOREIGN PATENT DOCUMENTS

EP    0 722 692    7/1996

(Continued)

OTHER PUBLICATIONS

Brody, J.E., "*Health Factor in Vegetables Still Elusive*," The New York Times, Section C, p. 1, Feb. 21, 1995.

(Continued)

*Primary Examiner*—Brian L. Casler
*Assistant Examiner*—Baisakhi Roy
(74) *Attorney, Agent, or Firm*—Holme Roberts & Owen LLP

(57) ABSTRACT

A method and apparatus are provided for Raman imaging of carotenoids and related chemical substances in biological tissue, such as macular pigments. The method and apparatus utilize the technique of resonance Raman spectroscopy to produce an image of the levels of carotenoids and similar substances in tissue. In this technique, light is directed upon the area of tissue which is of interest such as the retina of an eye. A small fraction of the scattered light is scattered inelastically, producing a carotenoid Raman signal which is at a different frequency than the incident light. The Raman signal is collected, filtered, and analyzed to determine the spatial position and intensity of the Raman signals in the inelastically scattered light. An image of the Raman signals is then produced on an output device, with the image representing the spatial distribution and concentration level of carotenoids in the tissue.

44 Claims, 7 Drawing Sheets

U.S. PATENT DOCUMENTS

| | | | | |
|---|---|---|---|---|
| 4,858,238 | A | 8/1989 | Cardimona | 372/3 |
| 5,034,228 | A | 7/1991 | Meybeck et al. | 424/401 |
| 5,124,313 | A | 6/1992 | Schaeffer et al. | 514/2 |
| 5,243,983 | A | 9/1993 | Tarr et al. | 128/633 |
| 5,275,168 | A | 1/1994 | Reintjes et al. | 128/665 |
| 5,290,605 | A | 3/1994 | Shapira | 424/439 |
| 5,303,026 | A | 4/1994 | Strobl et al. | 356/318 |
| 5,304,170 | A | 4/1994 | Green | 606/9 |
| 5,346,488 | A | 9/1994 | Prince et al. | 606/7 |
| 5,348,018 | A * | 9/1994 | Alfano et al. | 600/476 |
| 5,418,797 | A | 5/1995 | Bashkansky et al. | 372/3 |
| 5,421,337 | A | 6/1995 | Richards-Kortum et al. | 128/665 |
| 5,432,610 | A | 7/1995 | King et al. | 356/432 |
| 5,451,785 | A | 9/1995 | Faris | 250/330 |
| 5,452,723 | A | 9/1995 | Wu et al. | 128/664 |
| 5,553,616 | A | 9/1996 | Ham et al. | 128/633 |
| 5,556,612 | A | 9/1996 | Anderson et al. | 424/59 |
| 5,567,628 | A | 10/1996 | Tarcha et al. | 436/525 |
| 5,579,773 | A | 12/1996 | Vo-Dinh et al. | 128/665 |
| 5,590,660 | A | 1/1997 | MacAulay et al. | 128/664 |
| 5,643,623 | A | 7/1997 | Schmitz et al. | 426/73 |
| 5,657,754 | A | 8/1997 | Rosencwaig | 128/633 |
| 5,697,373 | A | 12/1997 | Richards-Kortum et al. | 128/664 |
| 5,733,507 | A | 3/1998 | Zakim | 422/101 |
| 5,873,831 | A * | 2/1999 | Bernstein et al. | 600/473 |
| 6,205,354 | B1 * | 3/2001 | Gellermann et al. | 600/477 |
| 6,690,966 | B1 * | 2/2004 | Rava et al. | 600/473 |
| 2003/0004419 | A1 * | 1/2003 | Treado et al. | 600/476 |

FOREIGN PATENT DOCUMENTS

| | | |
|---|---|---|
| WO | WO 92/10131 | 6/1992 |
| WO | WO 92/15008 | 9/1992 |

OTHER PUBLICATIONS

Bone, R.A., Landrum, J.T., and Cains, A, "*Optical Density Spectra of the Macular Pigment In Vivo and In Vitro*," Vision Res., vol. 32, No. 1, pp. 105-110, 1992.

Handelman, G.J., Snodderly, D.M., Krinsky, N.L., Russett, M.D., and Adler, A.J., "*Bilogical Control of Primate Macular Pigment*," Inv. Ophthalmol. Vis. Sci., vol. 32, No. 2, pp. 257-267, Feb., 1991.

Hammond, B.R., Fuld, K., and Curran-Celentano, J., "*Macular Pigment Density in Monozygotic Twins*," Invest. Ophthalmoo. Vis. Sci., vol. 36, No. 12, pp. 2531-2541, Nov., 1995.

Seddon, J.M., Ajani, U.A., Sperduto, R.D., Hiller, R., Blair, N., Burton, T.C., Farber, M.D., Gragoudas, E.S., Haller, Jr., Miller, D.T., Yannuzzi, L.A., and Willet, W., "*Dietary Carotenoids, Vitamins A, C and E, and Advanced Age-Related Macular Degneration*," J. Am. Med. Assoc., vol. 272, No. 18, pp. 1413-1420, Nov. 9, 1994.

Schalch, Wolfgang, "*Carotenoids in the Retina—A Review of Their Possible Role in Preventing or Limiting Damage Caused by Light and Oxygen*," Free Radicals and Aging, Basel, Switzerland: Birkhauser Verlag, pp. 280-298, 1992.

Tom C. Bakker Schut; Gerwin J. Puppels; Yvonne M. Kraan; Jan Greve; Louis L.J. Van Der Maas; and, Carl G. Figdor, "*Intracellular Carotenoid Levels Measured by Raman Microspectroscopy: Comparison of Lymphocytes from Lung Cancer Patients and Healthy Individuals*," Int. J. Cancer (Pred. Oncol): 74, 20-25 (1997).

Monika Gniadecka; Hans C. Wulf; Ole F. Nielsen; Daniel H. Christensen; and, Jana Hercogova, "*Distinctive Molecular Adnormalities in Benign and Malignant Skin Lesions: Sutdies by Raman Spectroscopy*," Photochemistry and Photobiology, 1997, 66(4): 418-423.

Christopher J. Frank; Douglas C.B. Redd; Ted S. Gansler; and, Richard L. McCreery, "*Characterization of Human Breast Biopsy Specimens with Near-IR Raman Spectroscopy*," Anal. Chem. 1994, 66, 319-326.

Berendshot, Tos T. J. M., et al., "*Influence of Lutein Supplementation on Macular Pigment, Assessed with Two Objective Techniques*," IOVS, Oct. 2000, vol. 41, No. 11, pp. 3322-3326.

Elsner, Ann E., et al, "*Foveal Cone Photopigment Distribution: Small Alterations Associated witih Macular Pigment Distribution*," IOVS, Nov. 1998, vol. 39, No. 12, pp. 2394-2404.

* cited by examiner

METHOD AND APPARATUS FOR RAMAN IMAGING OF MACULAR PIGMENTS

BACKGROUND OF THE INVENTION

1. Field of the Invention

The present invention relates generally to techniques for detecting and measuring levels of chemical compounds found in biological tissue. More specifically, the invention relates to a method and apparatus for Raman imaging of carotenoids and related chemical substances in biological tissue, such as macular carotenoid pigments, which can be used as a diagnostic aid for assessing the risk of disease.

2. Background Technology

Over the past few years, there has been increasing interest in studying the role of macular carotenoid pigments in the human retina. The macular pigments are comprised of the carotenoid species lutein and zeaxanthin, which are concentrated in the macula lutea. The macula lutea includes about a 5 mm diameter region of the retina essential for highest visual acuity and color vision. The macular pigments may be of fundamental importance in the treatment and prevention of age-related macular degeneration (AMD), a leading cause of blindness in the elderly. Absorbing in the blue-green spectral range, these pigments are thought to act as filters attenuating photochemical damage and/or image degradation caused by the phototoxic effect of blue/green light components reaching the retina. In addition, it is speculated that these pigments may play a protective role as free radical scavenging antioxidants.

To facilitate AMD research, a noninvasive, reliable and objective detection method for the macular pigments in the living human macula is needed. A noninvasive method for the measurement of carotenoid levels in the macular tissue of the eye is described in U.S. Pat. No. 5,873,831, the disclosure of which is herein incorporated by reference. In this method, levels of carotenoids and related substances are measured by a technique known as resonance Raman spectroscopy. This is a technique which can identify the presence and concentration (provided proper calibration is performed) of certain chemical compounds. In this technique, nearly monochromatic light is incident upon the sample to be measured, and the inelastically scattered light which is of a different frequency than the incident light is detected and measured. The frequency shift between the incident and scattered light is known as the Raman shift, and the shift corresponds to an energy which is the "fingerprint" of the vibrational or rotational energy state of certain molecules. Typically, a molecule exhibits several characteristic Raman active vibrational or rotational energy states, and the measurement of the molecule's Raman spectrum thus provides a fingerprint of the molecule, i.e., it provides a molecule-specific series of spectrally sharp vibration or rotation peaks. The intensity of the Raman scattered light corresponds directly to the concentration of the molecule(s) of interest. The resonance Raman technique described in U.S. Pat. No. 5,873,831 can be used to measure the levels of the carotenoids lutein and zeaxanthin, two chemicals which are associated with healthy macular tissue of the human eye.

Currently the most commonly used non-invasive method for measuring macular pigment levels is a psychophysical heterochromatic flicker photometric test involving color intensity matching of a light beam aimed at the fovea and another aimed at the perifoveal area. However, this method is subjective, time intensive, and requires an alert, cooperative subject with good visual acuity. Its repeatability depends on the understanding by the subject of the task involved. Thus, the usefulness of this method for assessing macular pigment levels in the elderly population most at risk for AMD and in subjects with macular pathologies is severely limited.

In another approach, an objective detection method for macular pigments is employed based on spectral fundus reflectance. This method has the advantage that it can be used both for the normal and abnormal human retina. In one variation of this method, the reflectance across the visual spectrum is measured quasi-simultaneously and estimates for macular pigment concentrations are obtained from a fit of the measured spectra with calculated spectra derived from a detailed optical model for foveal reflection and absorption. In imaging variations of this technique, an imaging fundus reflectometer or a modified scanning laser ophthalmoscope (SLO) is used to generate reflectance maps for two different scanning laser wavelengths, and the macular pigment distributions and concentrations are derived by digital image subtraction. The SLO measurements of macular pigments have been shown to provide more reliable results than spectral fundus reflectance or psychophysical measurements. However, the spectral fundus reflectance and SLO methodologies suffer from a lack of chemical specificity in their measurements due to the presence of multiple broadly absorbing substances in the retina.

SUMMARY OF THE INVENTION

The present invention is directed to a method and apparatus for Raman imaging of carotenoids and related chemical substances in biological tissue, such as macular carotenoid pigments. The method and apparatus utilize the technique of resonance Raman spectroscopy to produce an image of the levels and distributions of carotenoids and similar substances in tissue. In this technique, incident light is directed upon the area of tissue which is of interest such as the retina of an eye. The scattered light from the tissue includes a main portion of scattered light, which is of the same frequency as the incident light. A small fraction of the scattered light is scattered inelastically at different frequencies than the incident light, which is the Raman signal. The Raman scattered light is collected and separated, typically by wavelength selective filtering, and the resulting Raman signal is measured using a sensitive optical detection device. The Raman signal is then analyzed to determine the spatial position and intensity of the Raman signals in the inelastically scattered light. An image of the Raman signals is produced on an output device, with the image representing the spatial distribution and concentration level of carotenoids in the tissue.

The present invention can be used as a diagnostic aid for assessing the risk of disease such as degenerative eye diseases. The Raman imaging technique of the invention provides a non-invasive and rapid determination of the macular carotenoid levels in live subjects. The present invention thus offers valuable diagnostic information applicable to large populations which may help in assessing an individual's risk of developing age-related macular degeneration, and in determining protocols for prevention of the same.

These and other advantages and features of the present invention will become more fully apparent from the following description and appended claims, or may be learned by the practice of the invention as set forth hereinafter.

BRIEF DESCRIPTION OF THE DRAWINGS

In order to illustrate the manner in which the above-recited and other features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting in scope, the invention will be described and explained with additional specificity and detail through the use of the accompanying drawings in which.

DETAILED DESCRIPTION OF THE INVENTION

Figure 1:
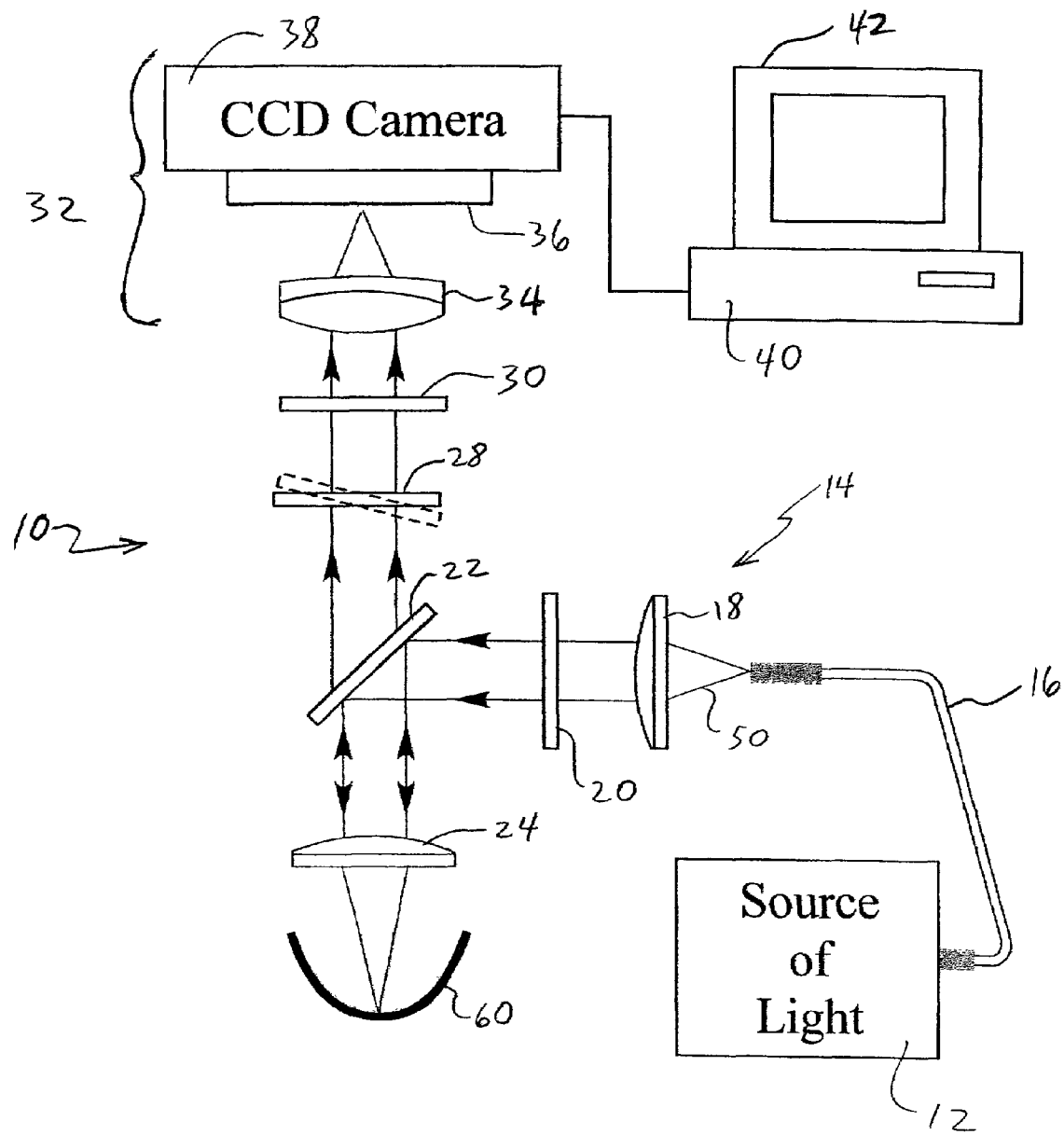
FIG. 1 is a schematic depiction of one embodiment of the apparatus of the present invention that employs a CCD array detector to acquire multiple Raman data points in parallel and is adapted for use with living or excised human tissue.

The present invention relates to a method and apparatus for Raman imaging of carotenoids and related chemical substances in biological tissue, such as macular carotenoid pigments, which can be used as a diagnostic aid for assessing the risk or presence of disease. The present invention is particularly suitable for assessing a subject's risk for suffering from diseases relating to the macular tissue in the eye. The Raman imaging technique of the invention provides a non-invasive, rapid, and objective determination of the macular carotenoid levels in live subjects. The present invention thus offers valuable diagnostic information applicable to large populations which may help in assessing an individual's risk of developing age-related macular degeneration, and in determining protocols for prevention of the same.

The present invention employs the technique of resonance Raman spectroscopy, which is used to identify and quantify the presence of carotenoids and similar substances in biological tissue, such as macular carotenoids in the eye, in order to produce a Raman image. In the case of carotenoids, the only current way to measure concentration is to use high pressure liquid chromatography (HPLC) chemical analysis, which has the disadvantage of requiring large volumes of biopsied tissue and tedious sample preparation. Additionally HPLC as well as traditional Raman spectroscopic methods are inherently single point measurements, and hence cannot produce a useful concentration map or image. The present invention has the further advantage of substantially, lower cost than traditional Raman spectroscopy instrumentation.

In the technique of the present invention, substantially monochromatic light is directed onto the tissue and the scattered light is then spectrally filtered and detected. The scattered light comprises both Rayleigh and Raman scattered light. The Rayleigh light is light which is elastically scattered, which means it is scattered at the same wavelength as the incident light. Most of the scattered light is scattered elastically. A small remainder of the light is scattered in an inelastic fashion, and is therefore of different frequencies than the incident light. This inelastically scattered light forms the Raman signal. The frequency difference between the incident light and the Raman scattered light is known as the Raman shift and is typically measured as a difference in wave numbers (or difference in frequencies or wavelengths). The magnitude of the Raman shifts is an indication of the type of chemical present, and the intensities of the Raman signal peaks correspond directly to the chemical concentration. The Raman shift is independent of the wavelength of incident light used, and hence, any strong and fairly monochromatic light source can be used in this technique.

One of the reasons why Raman spectroscopy is so useful is that specific wave number shifts correspond to certain modes of vibrational or rotational eigenstates associated with specific chemical structures, and hence provide a "fingerprint" of these chemical structures. For example, the macular carotenoids lutein and zeaxanthin exhibit characteristic Raman scattering, the results of which show up in distinct spectral positions, signal strengths, and spectral widths. Lutein and zeaxanthin exhibit strong characteristic Raman scattering signals near 1160 and 1525 $cm^{-1}$, and weaker signals near 1000 $cm^{-1}$. Further, isolation of any one or all resultant Raman peaks is possible. Lutein and zeaxanthin are polyene-like molecules featuring a Raman active, $\pi$-electron conjugated carbon backbone with alternating carbon-carbon double-(C=C) and single-(C—C) bonds. In both pigments, the electronic absorptions are strong, occur in a broad band (about 100 nm width) centered at about 450 nm, and show resolved vibronic substructure with a spacing of about 1400 $cm^{-1}$. Due to the ordering of the higher energy levels in these molecules, a fluorescence transition is parity forbidden. This allows one to perform resonance Raman scattering without potentially interfering fluorescence.

The technique of resonance Raman spectroscopy used in the present invention aids in overcoming the difficulties associated with measuring the inherently weak Raman signal. In resonance Raman spectroscopy, a light source of wavelength within the absorption bands corresponding to electronic transitions of the molecules of interest is utilized. By making the incident light close to resonant with the electronic absorption frequencies of the molecules of interest, the Raman signal is substantially enhanced, which provides the advantage of being able to use lower incident laser power, which in turn minimizes tissue damage, and also results in less stringent requirements for the sensitivity of the detection equipment.

Further details related to resonance Raman spectroscopy are described in U.S. Pat. No. 6,205,354, the disclosure of which is incorporated by reference herein.

The methods and apparatus of the invention are particularly useful in measuring macular carotenoids in live subjects utilizing resonance Raman spectroscopy. Retinal exposure to low light power generates a usable macular carotenoid Raman signal without significant damage to the macular tissue.

A method for imaging the spatial distribution and concentration level of macular carotenoids according to the invention comprises obtaining a light source that generates light at a wavelength that produces a Raman response with a wavelength shift for one or more macular carotenoids to be detected. Light is directed from the light source onto macular tissue of an eye for which macular carotenoid levels are to be measured. The light scattered from the macular tissue is collected, with the scattered light including elastically and inelastically scattered light. The inelastically scattered light has a plurality of Raman signals corresponding to the one or more macular carotenoids. The elastically scattered light is filtered out, and the spatial position and intensity of the Raman signals in the inelastically scattered light is analyzed. An image of the Raman signals is then produced, with the image representing the spatial distribution and concentration level of the one or more macular carotenoids in the macular tissue.

It should also be understood that the methods and apparatus of the invention may be utilized to detect other materials present in retinal tissue, or to detect carotenoids and related substances in other biological tissues.

Referring to the drawings, wherein like structures are labeled with like reference designations, FIG. 1 is a schematic depiction of one embodiment of the apparatus of the present invention, generally labeled 10. The apparatus 10 is configured to measure and image carotenoid levels in tissue, such as macular carotenoids, using resonant Raman spectroscopy. The apparatus 10 includes a light source 12, which in one embodiment can be a mercury arc lamp. Alternatively, light source 12 may comprise other devices for generating nearly monochromatic light such as a low power solid state or argon ion laser. The light source 12 is configured to generate light in a wavelength that overlaps the absorption bands of the carotenoids of interest. The light from light source 12 preferably has an intensity that does not destroy the macular tissue nor substantially alter carotenoid levels in the macular tissue.

The light source 12 is in optical communication with a light delivery and collection means such as an optical module 14, which can include various optical components for directing light to the tissue to be measured and collecting the scattered light from the tissue. As shown in FIG. 1, optical module 14 can be in optical communication with light source 12 through a light transmission device such as a fiber optic bundle 16 or other suitable light transmission device. The light that is transmitted into optical module 14 is transmitted or reflected by various optical components therein, including a diffuser (not shown), a collimating condenser lens 18, a band pass filter 20, a dichroic or holographic beam splitter 22, and a lens 24, which focuses the light onto the subject tissue. The lens 24 also collects the light scattered back from the subject tissue, and such light is transmitted through beam splitter 22.

The transmitted light is filtered to select a Raman peak, for example the C=C stretch frequency of a carotenoid of interest, by a wavelength selective means for selecting Raman shifted light from the collected scattered light. For example, the wavelength selective means can include one or more wavelength selective devices, such as a narrow band interference filter 28 and a broad band interference filter 30 as shown in FIG. 1, or other optical filter configurations such as a fully blocked narrow band filter. In addition, the wavelength selective devices can be acousto-optic tunable filters (AOTFs) or dispersion based devices (e.g., a spectrograph), and the like.

The filter 28 can be angle tuned to alternately transmit the Raman scattered light at a wavelength position that corresponds to the Raman peak ("on peak" position), or to transmit the background light at a wavelength position that just misses the Raman peak ("off peak" position). Alternatively, the wavelength selective means can be adapted to simultaneously transmit Raman shifted light at an on peak wavelength position and to transmit light at an off peak wavelength position. The bandwidth of filter 28 is chosen to match the bandwidth on of the excitation light in order to maximize the Raman signal throughput. When beam splitter 22 is a holographic beam splitter, beam splitter 22 can be selected to reflect about 99% of the excitation light and transmit about 90% of the Raman shifted light.

The optical module 14 is in optical communication with a detection means such as an optical detection device 32, which is capable of measuring the intensity of the Raman scattered light as a function of frequency in the frequency range of interest such as the frequencies characteristic of carotenoids in the eye or other tissue. The optical detection device 32 can include, for example, a camera lens 34 used to image the Raman scattered light from macular tissue onto an optical detector array such as a pixel array 36 of a CCD (charge coupled device) camera 38.

An analyzing means for determining the spatial position and intensity of Raman signals in the Raman shifted light is operatively connected to optical detection device 32. The analyzing means can be a computer or other data processing device, such as a personal computer 40. The detected light is converted by optical detection device 32 into a signal which is transmitted to computer 40 for processing the signal data. For example, the signal data can be processed with software that produces an output image of the Raman signal levels received by the CCD pixel array versus spatial position. Such an output image can be displayed as grayscale or pseudo (false) color "en face" maps and/or as topographical representations ("surface plots"). An output means such as various output devices can be used to produce the image of the Raman signals, with the image representing the spatial distribution and concentration level of the one or more carotenoids. The output device can be used to display or print the Raman image. For example, the image can be displayed on a visual display monitor such as a computer monitor 42, or sent to a printer connected to computer 40 for printing the image.

During operation of apparatus 10, a light beam 50 is generated from light source 12 and is directed through fiber optic bundle 16 into optical module 14. For example, light beam 50 can be generated in a wavelength range from about 350 nm to about 550 nm, and preferably about 425 nm to about 500 nm. Such wavelengths generally correspond to the absorption characteristics of macular carotenoids. The light beam 50 can be generated with an exposure spot size of about 5 microns to about 10 mm, and preferably about 10 microns to about 5 mm. The light beam 50 can also be generated to have an exposure time of about 0.001 seconds to about 100 seconds, and preferably about 1 second to about 10 seconds. The power density or light intensity of beam 50 can be about 1 mW/cm$^2$ to about 200 mW/cm$^2$, and preferably about 5 mW/cm$^2$ to about 50 mW/cm$^2$.

The light beam 50 is sent through a diffuser and collimated by condenser lens 18 in optical module 14. The light beam 50 is then spectrally filtered by passing through filter 20, is reflected by beam splitter 22, and is projected by lens 24 onto the subject tissue such as the fovea of a subject eye 60. Placement of the light in the eye tissue may be verified by direct confirmation by an operator via a suitable optical system. The light is preferably selectively directed in order to cover a major area of macular carotenoid pigment deposition.

The light scattered back from the subject tissue such as eye 60 is collected by lens 24, transmitted through beam splitter 22, and is filtered by passing through interference filters 28 and 30. The filtered light then passes to optical detection device 32, where lens 34 focuses the Raman scattered light onto detector pixel array 36 of CCD camera 38. The detected light is then converted into a signal that is transmitted to computer 40 for processing the signal data, where Raman-shifted signal levels (i.e., the difference between Raman peak signals and background scattered light) are determined. An image of the Raman signal levels, representing the spatial distribution and concentration of carotenoids in the subject tissue, is then output by computer 40 to a visual display or to a printer.

Figure 2:
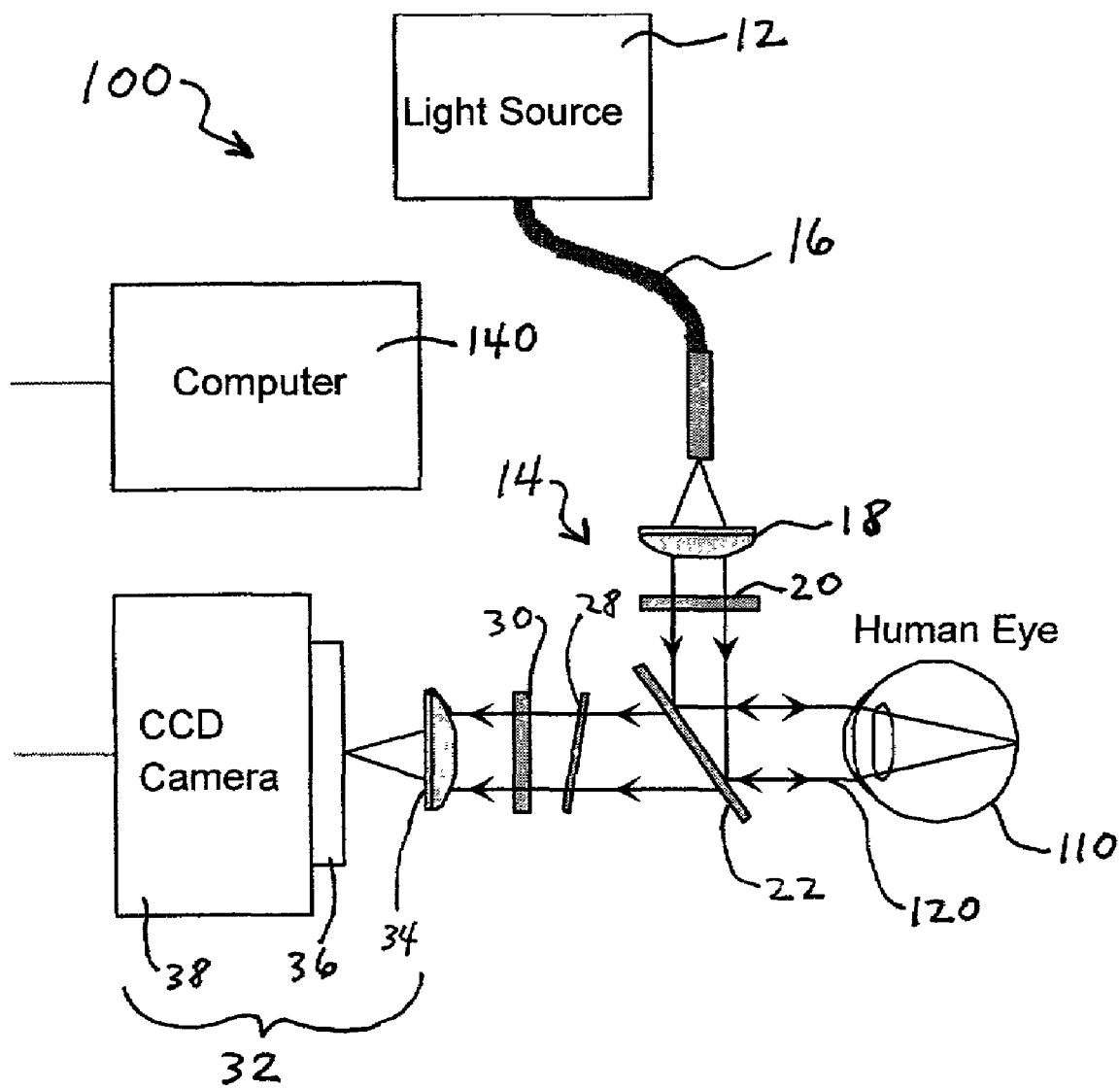
FIG. 2 is a schematic depiction of another embodiment of the apparatus of the present invention that employs a CCD array detector to acquire Raman data in parallel and is adapted for use with living human eyes.

FIG. 2 is a schematic depiction of another embodiment of the apparatus of the present invention, generally labeled 100, for measuring and imaging carotenoid levels in tissue, such as macular carotenoids in living eyes. The apparatus 100 includes similar components as discussed above for apparatus 10, including a light source 12, and an optical module 14 in optical communication with light source 12 through a fiber optic bundle 16. The orientation of light source 12 used in apparatus 100 is changed with respect to the orientation used in apparatus 10 in order to make apparatus 100 more suitable for measuring living eyes of subject patients. The optical module 14 includes various optical components such as a collimating condenser lens 18, a band pass filter 20, and a dichroic or holographic beam splitter 22. The lens 24 used in apparatus 10 is not needed in apparatus 100 since the function of lens 24 is replaced by the human eye lens located in living human eye 110. Thus, a light beam 120 can be projected onto the macular area of eye 110 by having the subject patient fixate on the light.

The light that is scattered back from eye 110 during operation of apparatus 100 is transmitted through beam splitter 22. The transmitted light is filtered to select a Raman peak, for example the C=C stretch frequency of a carotenoid of interest, by a wavelength selective means for selecting Raman shifted light from the collected scattered light. For example, the wavelength selective means can include a narrow band interference filter 28 and a broad band interference filter 30, or other optical filter configurations.

The optical module 14 of apparatus 100 is in optical communication with an optical detection device 32, which can include, for example, a camera lens 34 used to image the Raman scattered light from the macular tissue onto a pixel array 36 of a CCD camera 38. A computer 140 or other data processing device is operatively connected to optical detection device 32 in order to determine the spatial position and intensity of Raman signals in the Raman shifted light. The computer 140 typically includes one or more output devices such as a visual display and printer for producing an image of the Raman signal levels.

Figure 3:
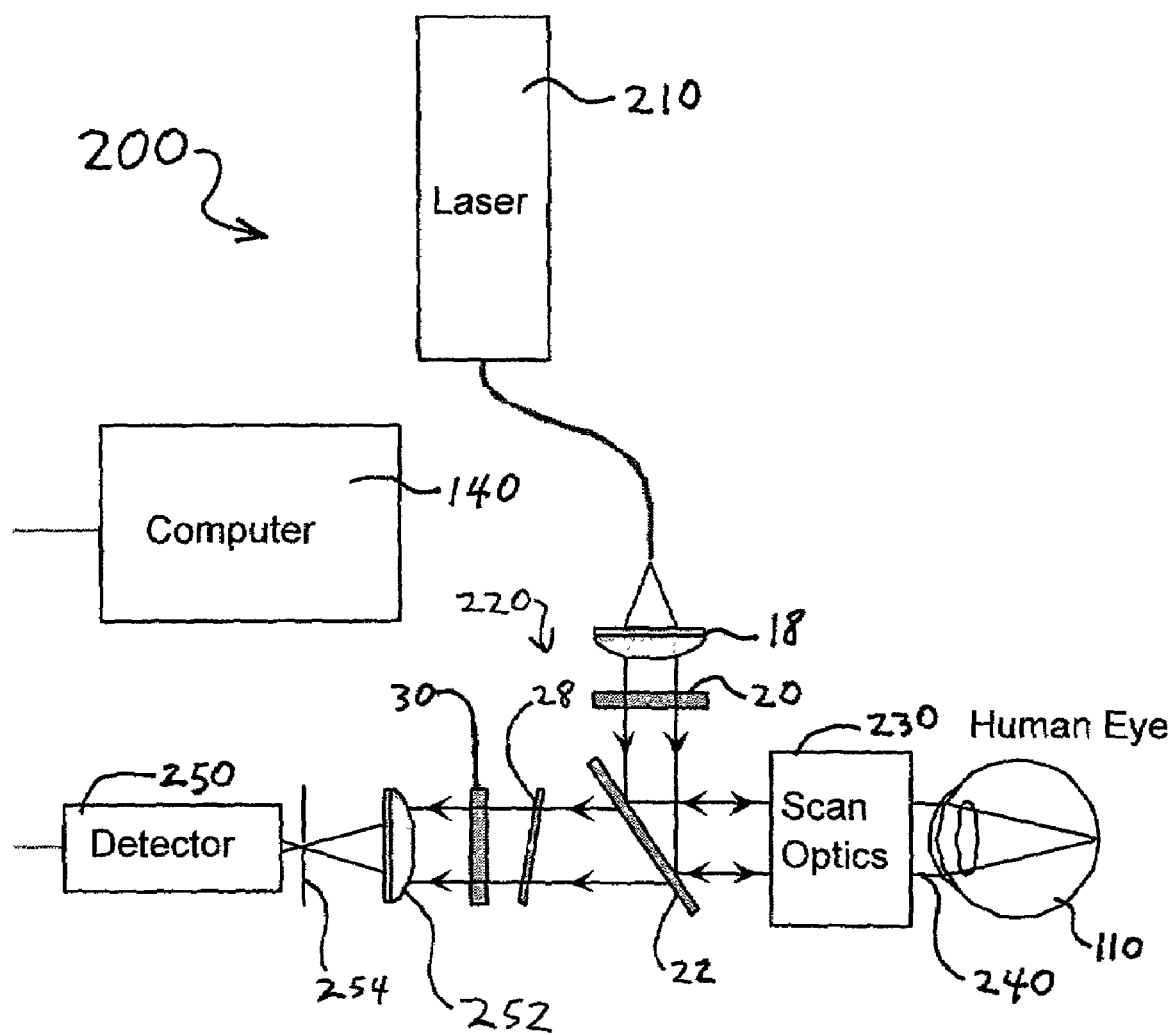
FIG. 3 is a schematic depiction of a further embodiment of the apparatus of the present invention that employs a discrete photo detector to acquire Raman data in series (point by point) and is adapted for use with living human eyes.

FIG. 3 is a schematic depiction of a further embodiment of the apparatus of the present invention, generally labeled 200, for measuring and imaging carotenoid levels in tissue, such as macular carotenoids. The apparatus 200 is configured to use serial (point-by-point) data collection techniques. The apparatus 200 includes a light source that is preferably a laser 210, and an optical module 220 in optical communication with laser 210. The optical module 220 comprises optical components such as those discussed previously for optical module 14 of apparatus 10, including a collimating condenser lens 18, a band pass filter 20, and a dichroic or holographic beam splitter 22.

In addition, optical module 210 includes a scanning-type instrument such as scan optics 230 positioned between beam splitter 22 and the location for living human eye 110. The scan optics 230 steers the light beam 240 from laser 210 so as to scan the beam in an x-y grid across the macular area of eye 110. The scan optics 230 can use a mirror configuration or other standard techniques for steering a beam, such as raster scanning. The scanning of the beam allows for serial data collection techniques to be employed in which data is generated based on each discrete scanned point in the macular area.

Each of the beams of light that is scattered back from eye 110 during operation of apparatus 200 is transmitted through beam splitter 22. The transmitted light is filtered to select a Raman peak, for example the C=C stretch frequency of a carotenoid of interest, by a wavelength selective means. For example, the wavelength selective means can include a narrow band interference filter 28 and a broad band interference filter 30, or other optical filter configurations.

The optical module 220 of apparatus 200 is in optical communication with a detection means such as a discrete photo detector 250, which can be a photomultiplier tube (PMT) or an avalanche photo diode (APD). A lens 252 is configured to focus the Raman scattered light from the macular tissue through a pin hole aperture 254 and onto photo detector 250. A computer 140 or other data processing device is operatively connected to photo detector 250 in order to record the intensity of Raman signals in the Raman shifted light at each scanned point in the macula.

During operation of apparatus 200, the light beams from laser 210 are sequentially scanned from point to point across the macular tissue by scan optics 230, generating Raman data for processing into an image of the tissue. Alternatively, the whole optical assembly of apparatus 200 can be configured to sequentially scan the light beams from point to point across the macular tissue.

It should be understood that the embodiments of FIGS. 1–3 can be modified such that wavelength selection is carried out on the excitation (light source) side of the apparatus rather than on the detection side of the apparatus as shown. It does not matter whether the wavelength selective device is on the detection side or on the excitation side since the main concern is to measure the difference between Raman shifted light ("on peak") and background light ("off peak") for each image data point. For instance, a fixed, non-tuning filter can be positioned between the beam splitter and the detector, and the light source filter can be an angle-tuned wavelength selective filter. This would alternately shift the Raman peak in and out of the pass band of the non-tuning filter, providing the same ability to calculate the difference between Raman scattered light and background light for each image data point.

The method and apparatus of the present invention facilitate simple and low cost acquisition of spectroscopic data based on the resonant Raman effect. The resulting data is used to produce high spatial resolution images based on the concentration and distribution of selected chemical compounds. Such images produced by the present invention can allow correlations between macular pigment profiles and clinical as well as basic biology applications.

The capability of the present invention to produce an imaging mode by Raman detection provides many further benefits and advantages. The present invention can be used in the study of age-related macular degeneration and other inherited and acquired retinal degenerations. For example, the invention can be used in population studies to give insight into individual variations in the spatial profiles of visual and macular pigment distributions. In clinical research this would have implications for retinal senescence and could correlate the spatial extent of visual loss in AMD patients with macular pigment spatial profiles. For example, the present invention can potentially be used in a rapid screening method to measure macular pigments in large populations at risk for vision loss from AMD. In basic research, individual spatial variations of macular pigment could be of consequence for models of early visual processing and for quantitative models of color vision.

The present invention also provides detailed information with respect to individual differences in macular pigment absolute levels as well as spatial profiles. In clinical applications, such information can be used to correlate with retinal pathologies, lifestyle variables such as diet and smoking, and anatomical parameters such as widths of the foveal depression, size of the avascular zone, retinal thickness, and cone density.

The invention can also be applied in a clinical setting to provide non-contact, non-invasive diagnostics of certain other diseases. For example, the concentration and distribution of certain carotenoids and related compounds have been postulated to be indicative of the presence or risk of various diseases, thus the invention may be used as a diagnostic tool to quickly and painlessly screen for these diseases, or follow the effectiveness of their treatment.

It should be understood that the present invention is not limited to imaging of macular carotenoids. The method of the present invention is also applicable to the measurement of β-carotene and pharmacological agents such as canthaxanthin, astaxanthin, chloroquine, hydroxychloroquine, thioridazine, and tamoxifen, which are concentrated and deposited within the retina. In addition, the present invention can be used to image carotenoids and other related substances in the skin or other tissue.

The following examples are given to illustrate the present invention, and are not intended to limit the scope of the invention.

EXAMPLE 1

An experimental apparatus similar to that shown in FIG. 1 discussed previously and suitable for Raman measurements of carotenoids in biological tissue such as the eye was assembled and operated as follows. Light from a mercury arc lamp was routed via a fiber optic bundle into a light delivery and collection module. The light from the lamp was a narrow bandwidth blue light. Inside the module, the light was sent through a diffuser, collimated by a condenser lens, spectrally filtered further at 488 nm with a 1.25 nm band pass filter, reflected by a holographic beam splitter, and projected by a lens (30 mm focal length) onto about a 4 mm diameter spot centered on the fovea of an excised eyecup. The blue-filtered excitation light power at the fovea was 320 µW, corresponding to an excitation light intensity of 2.55 mW/cm². The light scattered back from the retina was collected by the lens, transmitted through the beam splitter, and filtered at the C=C stretch frequency (527 nm in the case of 488 nm excitation). The filtering was achieved with a combination of a narrow band and a broad band interference filter (with bandwidths of 1 nm and 10 nm, respectively).

A camera lens was used to image the Raman scattered light onto the 375×241 pixel array of a CCD camera (Santa Barbara Imaging Group, Inc., Model ST-6uv, pixel size 23×27 µm), permitting digital image acquisition with 16 bits of gray scale. The narrow band filter was angle tuned to alternately transmit the Raman scattered light at 527 nm ("on peak" position) or to transmit the background light at a wavelength position of 529 nm, just missing the Raman peak ("off peak" position). The bandwidth of the narrow band filter was chosen to match the bandwidth of the excitation light in order to maximize the Raman signal throughput. A holographic beam splitter was employed that reflects about 99% of the excitation light and transmits about 90% of the Raman shifted light. The reflectivities of the beam splitter and narrow/broad band filters combined to provide an extinction of $10^{-6}$ at the Raman excitation wavelength (488 nm).

A Raman image was generated showing the spatial distribution and concentration level of macular carotenoid pigments in the human retina. The Raman image was generated by using the difference between two image data sets. A first data set was obtained with the narrow band filter tuned to the "on peak" position and a second data set was obtained with this filter tuned to the "off peak" position. For both data sets, identical exposure times (25 seconds) and imaging conditions were used. All data sets were processed with software obtained from the National Institutes of Health (NIH Image 1.62), which allowed the display of the Raman signal levels received by the CCD pixel array as a function of spatial position. Grayscale and pseudo (false) color "en face" maps and topographical representations (surface plots) were generated.

EXAMPLE 2

Figure 4:
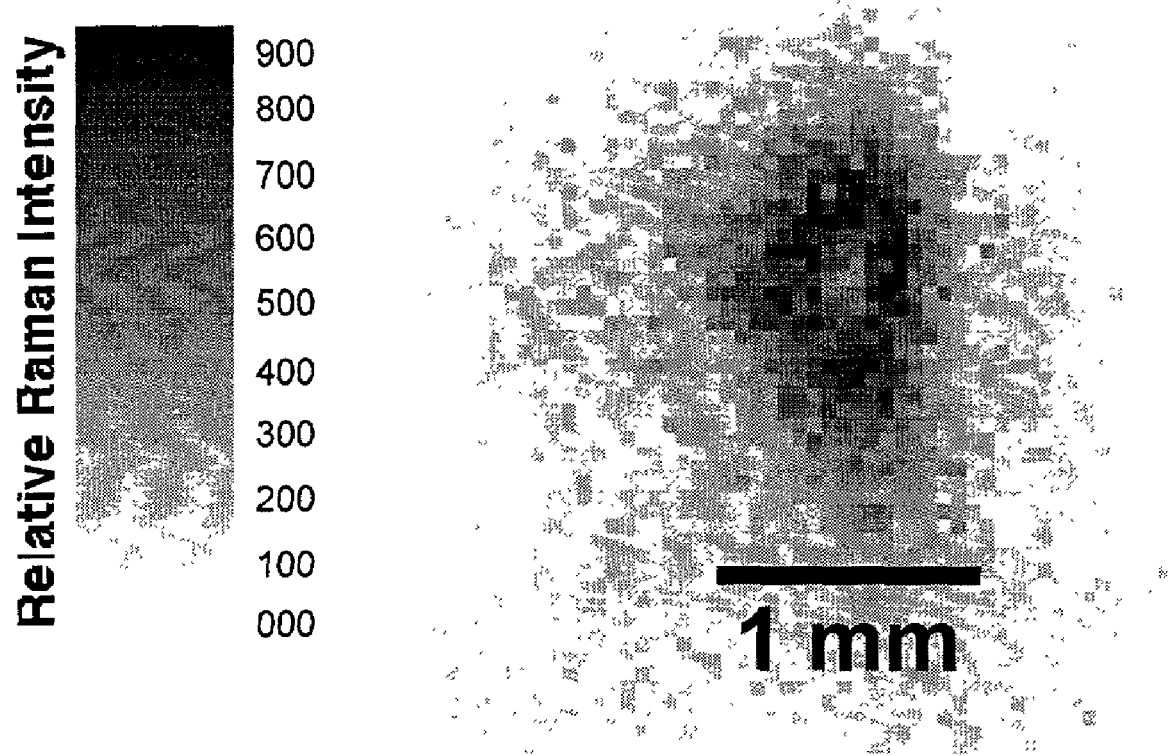
FIG. 4 is an en face Raman image of a human fovea in the macular region of one excised human eye cup mapping the macular pigment distribution.

Twelve excised post-mortem human eye cup samples were measured using the apparatus described in Example 1, all yielding significantly varying Raman images, both in regard to absolute levels as well as spatial variation. Such variations, included rotational asymmetry, varying spatial extent (width) of macular pigment distribution, and in some cases even depletion of central macular pigment levels. The results of one sample measurement is shown in FIG. 4 as en face map, depicting the Raman image of macular pigment distribution in a human fovea. The number of Raman data points was 6,232 and the spatial resolution on the retina was 55×43 microns. The relative Raman signal intensity is grayscale coded according to the scale shown at the left side of FIG. 4. The image of FIG. 4 reveals a macular pigment distribution which is both asymmetric and which reaches maximum levels not in the center but at an eccentricity. The macular pigment levels varied by at least one order of magnitude comparing the noise floor and the maxima of the distribution.

Figure 5:
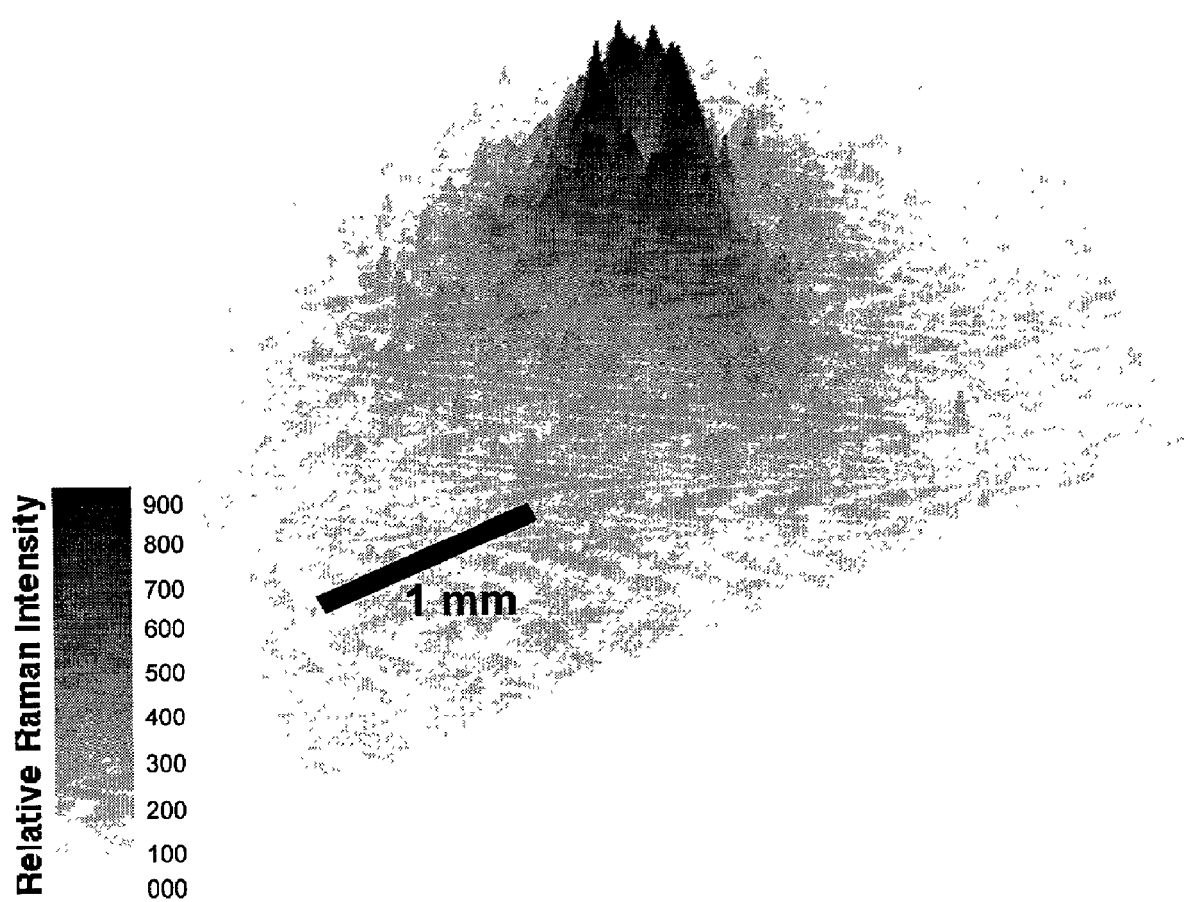
FIG. 5 is a surface plot of the Raman image of FIG. 4, depicting the topology of the macular pigment distribution.

In FIG. 5, the data of FIG. 4 is depicted as a surface plot image to emphasize the topology of the macular pigment distribution. The relative Raman signal intensity is grayscale coded according to the scale shown at the left side of FIG. 5. The Raman image clearly reveals an asymmetric, cone-shaped pigment distribution, with high pigment levels concentrated over a central area (full width at half maximum about 1 mm), and rapidly decreasing pigment levels toward the wings of the cone. The center of the distribution appears to have a 250 µm diameter depletion in the pigment density with a "hole" depth of about half the pigment concentration.

Figure 6:
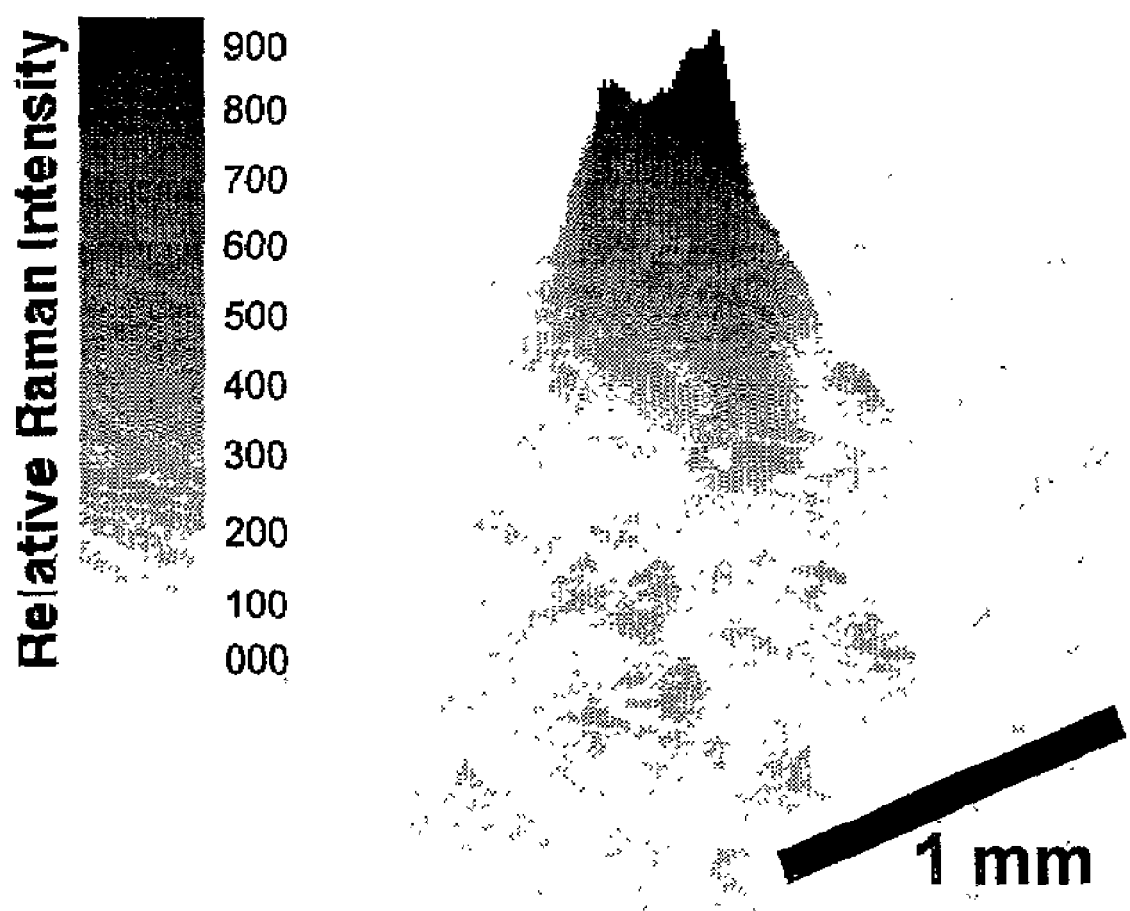
FIG. 6 is a surface plot of a Raman image of macular pigment distribution in a human fovea of another excised human eye cup.

Another sample measurement using the apparatus described in Example 1 produced a Raman image of macular pigment distribution in a human fovea as shown in FIG. 6, which is a topographical surface plot image. The Raman image of FIG. 6 reveals a ridge shaped pigment distribution, with high pigment levels concentrated over a smaller area (full width at half maximum about 0.25 mm) without any central depletion. Even though the peak macular pigment level in shown FIG. 6 is almost as high as that in FIG. 5, the total amount of pigment in this fovea is only about one third as much.

Figure 7:
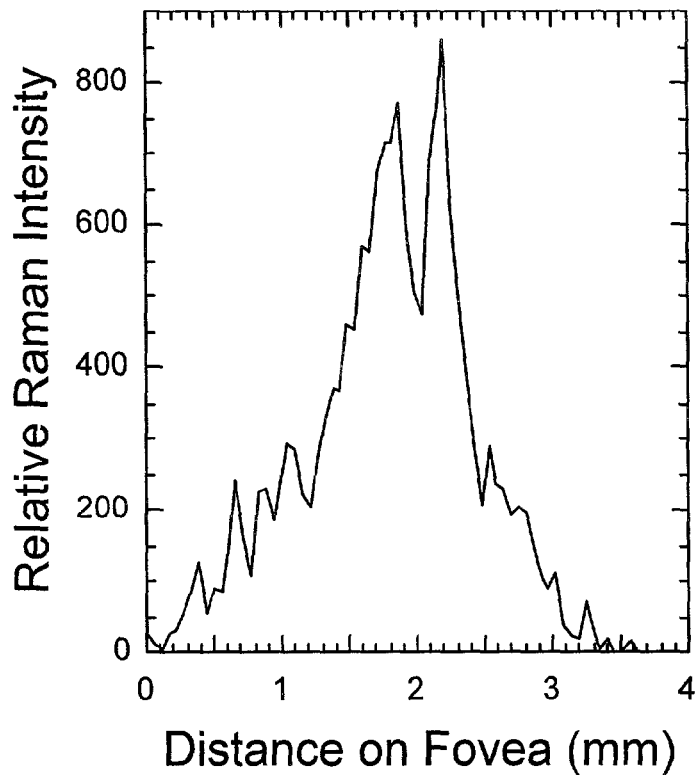
FIGS. 7 and 8 are line plots showing the spatial variation of the Raman signal intensity for the two pigment distribution images of FIGS. 5 and 6, respectively.
Figure 8:
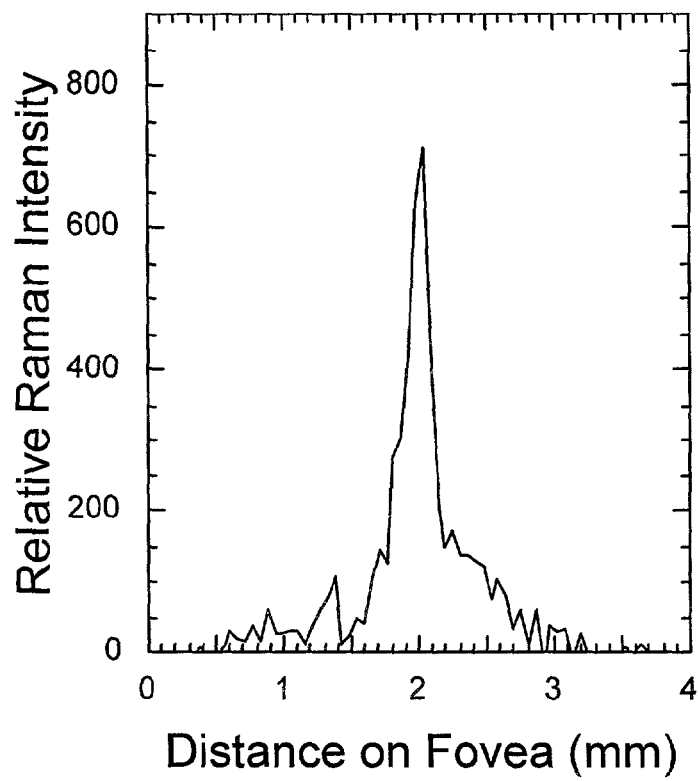

FIGS. 7 and 8 are line plots showing the spatial variation of the Raman signal intensity for the two pigment distribution images of FIGS. 5 and 6, respectively. The plots of FIGS. 7 and 8 were generated along a horizontal line running through the centers of the distributions shown in FIGS. 5 and 6.

The images of FIGS. 4–6 demonstrate that the resonance Raman spectroscopy technique of the present invention is capable of imaging physiological macular pigment distributions in human eye cups with good signal-to-noise ratio using Raman excitation with a non-laser light source. Such Raman imaging provides micron-scale spatial information on macular pigment distribution as well as quantification of pigment levels.

The present invention may be embodied in other specific forms without departing from its spirit or essential characteristics. The described embodiments are to be considered in all respects only as illustrative and not restrictive. The scope of the invention is therefore indicated by the appended claims rather than by the foregoing description. All changes that come within the meaning and range of equivalency of the claims are to be embraced within their scope.

What is claimed is:

1. A method for imaging the spatial distribution and concentration level of macular carotenoids, the method comprising:
    obtaining a light source that generates light at a wavelength that produces a Raman response with a wavelength shift for one or more macular carotenoids to be detected;
    directing light from the light source onto macular tissue of an eye for which macular carotenoid levels are to be measured, wherein the light directed onto the macular tissue of the eye has an intensity that does not destroy the macular tissue;
    collecting light scattered from the macular tissue, the scattered light including elastically and inelastically scattered light, the inelastically scattered light having a plurality of Raman signals corresponding to the one or more macular carotenoids;
    selectively removing the elastically scattered light;
    analyzing the spatial position and intensity of the Raman signals in the inelastically scattered light; and
    producing an image of the Raman signals, the image representing the spatial distribution and concentration level of the one or more macular carotenoids in the macular tissue at a plurality of data points.

2. The method of claim 1, wherein the light source generates light at a wavelength that overlaps the absorption bands of the one or more macular carotenoids to be detected.

3. The method of claim 1, wherein the light source generates light in a wavelength range from about 350 nm to about 550 nm.

4. The method of claim 1, wherein the light from the light source has an intensity that does not destroy the macular tissue and does not substantially alter carotenoid levels in the macular tissue.

5. The method of claim 1, wherein the light source generates light at an exposure spot size of about 5 microns to about 10 mm.

6. The method of claim 1, wherein the light source generates light with an exposure time of about 0.001 to about 100 seconds.

7. The method of claim 1, wherein the macular tissue resides in a live subject.

8. The method of claim 1, wherein the inelastically scattered light is analyzed at frequencies characteristic of macular carotenoids.

9. The method of claim 1, wherein the image of the Raman signals is an en face map.

10. The method of claim 1, wherein the image of the Raman signals is a topographical surface plot.

11. A method for imaging the spatial distribution and concentration level of carotenoids in biological tissue, the method comprising:
    obtaining a light source that generates light at a wavelength that produces a Raman response with a wavelength shift for one or more carotenoids to be detected;
    directing light from the light source onto biological tissue for which carotenoid levels are to be measured, wherein the light directed onto the biological tissue has an intensity that does not destroy the biological tissue;
    collecting light scattered from the biological tissue, the scattered light including elastically and inelastically scattered light, the inelastically scattered light having a plurality of Raman signals corresponding to the one or more carotenoids;
    selectively removing the elastically scattered light;
    analyzing the spatial position and intensity of the Raman signals in the inelastically scattered light; and
    producing an image of the Raman signals, the image representing the spatial distribution and concentration level of the one or more carotenoids in the biological tissue at a plurality of data points.

12. A method for imaging the spatial distribution and concentration level of selected materials in retinal tissue, the method comprising:
    obtaining a light source that generates light at a wavelength that produces a Raman response with a wavelength shift for a material to be detected;
    directing light from the light source onto retinal tissue of an eye for which levels of the material are to be measured;
    collecting light scattered from the retinal tissue, the scattered light including elastically and inelastically scattered light, the inelastically scattered light having a plurality of Raman signals corresponding the material;
    selectively removing the elastically scattered light;
    analyzing the spatial position and intensity of the Raman signals in the inelastically scattered light; and
    producing an image of the Raman signals, the image representing the spatial distribution and concentration level of the material in the retinal tissue at a plurality of data points.

13. An imaging apparatus, comprising:
    a light source that generates light at a wavelength giving a Raman response with a wavelength shift for one or more carotenoids to be detected wherein the light source generates light at a wavelength that overlaps the absorption bands of the one or more carotenoids to be detected;
    a light delivery and collection means in optical communication with the light source for directing light onto tissue and collecting scattered light from the tissue;
    wavelength selective means for selecting Raman shifted light from collected scattered light;

detection means for measuring the intensity of the Raman shifted light at frequencies characteristic of the one or more carotenoids to be detected;

analyzing means for determining the spatial position and intensity of Raman signals in the Raman shifted light; and output means for producing an image of the Raman signals, the image representing the spatial distribution and concentration level of the one or more carotenoids at a plurality of data points.

14. The imaging apparatus of claim 13, wherein the light source generates light in a wavelength range from about 350 nm to about 550 nm.

15. The imaging apparatus of claim 13, wherein the light source generates light at an exposure spot size of about 5 microns to about 10 mm.

16. The imaging apparatus of claim 13, wherein the light source generates light with an exposure time of about 0.001 to about 100 seconds.

17. The imaging apparatus of claim 13, wherein the wavelength selective means is adapted to be angle tuned to alternately transmit Raman shifted light at an on peak wavelength position, or to transmit light at an off peak wavelength position.

18. The imaging apparatus of claim 13, wherein the wavelength selective means is adapted to simultaneously transmit Raman shifted light at an on peak wavelength position and to transmit light at an off peak wavelength position.

19. The imaging apparatus of claim 13, wherein the detection means comprises an optical detector array on a charge coupled device camera.

20. The imaging apparatus of claim 13, wherein the detection means comprises a discrete photo detector.

21. The imaging apparatus of claim 13, wherein the analyzing means comprises a computer.

22. The imaging apparatus of claim 13, wherein the output means comprises a visual display monitor.

23. The imaging apparatus of claim 13, wherein the output means comprises a printer.

24. The imaging apparatus of claim 13, wherein the image produced by the output means is an en face map.

25. The imaging apparatus of claim 13, wherein the image produced by the output means is a topographical surface plot.

26. An imaging apparatus, comprising:
a light source that generates light at a wavelength giving a Raman response with a wavelength shift for one or more carotenoids to be detected wherein the light source generates light at a wavelength that overlaps the absorption bands of the one or more carotenoids to be detected;

an optical module in optical communication with the light source, the optical module configured to direct light onto tissue and collect scattered light from the tissue;

one or more wavelength selective devices configured to select and transmit Raman shifted light from collected scattered light;

an optical detection device configured to measure the intensity of Raman shifted light at frequencies characteristic of the one or more carotenoids to be detected;

a data processing device operatively connected to the optical detection device, the data processing device adapted to determine the spatial position and intensity of Raman signals in the Raman shifted light; and an output device adapted to display an image of the Raman signals, the image representing the spatial distribution and concentration level of the one or more carotenoids at a plurality of data points.

27. The imaging apparatus of claim 26, wherein the light source comprises a mercury arc lamp.

28. The imaging apparatus of claim 26, wherein the light source comprises an argon ion laser.

29. The imaging apparatus of claim 26, wherein the light source generates light in a wavelength range from about 350 nm to about 550 nm.

30. The imaging apparatus of claim 26, wherein the optical communication between the light source and the optical module is provided by a fiber optic bundle.

31. The imaging apparatus of claim 26, wherein the optical module comprises:
a collimating condenser lens;
a band pass filter in optical communication with the condenser lens; and
a dichroic or holographic beam splitter in optical communication with the band pass filter.

32. The imaging apparatus of claim 31, wherein the optical module further comprises a lens in optical communication with the beam splitter and configured to focus light onto the tissue and collect light scattered back from the tissue.

33. The imaging apparatus of claim 31, wherein the optical module further comprises a scanning-type instrument in optical communication with the beam splitter and configured to sequentially scan a light beam from point to point across the tissue.

34. The imaging apparatus of claim 26, wherein the one or more wavelength selective devices comprise a narrow band interference filter and a broad band interference filter.

35. The imaging apparatus of claim 34, wherein the narrow band interference filter is adapted to be angle tuned.

36. The imaging apparatus of claim 26, wherein the one or more wavelength selective devices comprise a fully blocked narrow band filter.

37. The imaging apparatus of claim 26, wherein the one or more wavelength selective devices are selected from the group consisting of acousto-optic tunable filters, and dispersion based devices.

38. The imaging apparatus of claim 26, wherein the optical detection device comprises an optical detector array on a charge coupled device camera.

39. The imaging apparatus of claim 26, wherein the optical detection device comprises a discrete photo detector.

40. The imaging apparatus of claim 39, wherein the discrete photo detector is selected from the group consisting of a photomultiplier tube, and an avalanche photo diode.

41. The imaging apparatus of claim 39, further comprising a pinhole aperture disposed in front of the discrete photo detector.

42. The imaging apparatus of claim 26, wherein the data processing device comprises a computer.

43. The imaging apparatus of claim 26, wherein the output device comprises a visual display monitor.

44. The imaging apparatus of claim 26, wherein the output device comprises a printer.

* * * * *